(12) United States Patent
Burns

(10) Patent No.: US 7,032,607 B2
(45) Date of Patent: Apr. 25, 2006

(54) CAPILLARY REACTOR DISTRIBUTION DEVICE AND METHOD

(75) Inventor: John Robert Burns, Sunderland (GB)

(73) Assignee: Protensive Limited, Cambridge (GB)

( * ) Notice: Subject to any disclaimer, the term of this patent is extended or adjusted under 35 U.S.C. 154(b) by 449 days.

(21) Appl. No.: 10/220,785

(22) PCT Filed: Mar. 1, 2001

(86) PCT No.: PCT/GB01/00848

§ 371 (c)(1),
(2), (4) Date: Jan. 21, 2003

(87) PCT Pub. No.: WO01/64332

PCT Pub. Date: Sep. 7, 2001

(65) Prior Publication Data

US 2003/0145894 A1 Aug. 7, 2003

(30) Foreign Application Priority Data

Mar. 2, 2000 (GB) .............................. 0004958

(51) Int. Cl.
*F15C 1/06* (2006.01)
*F15B 21/00* (2006.01)

(52) U.S. Cl. .................. 137/14; 137/807; 137/833; 251/367

(58) Field of Classification Search .............. 137/14, 137/833, 807; 251/367
See application file for complete search history.

(56) References Cited

U.S. PATENT DOCUMENTS

| 4,676,274 | A | * | 6/1987 | Brown | ................ 137/806 |
|---|---|---|---|---|---|
| 5,789,045 | A | * | 8/1998 | Wapner et al. | ............. 428/34.4 |
| 5,921,678 | A | | 7/1999 | Desai et al. | |
| 5,927,852 | A | | 7/1999 | Serafin | |
| 6,046,056 | A | * | 4/2000 | Parce et al. | .................. 436/514 |
| 6,068,752 | A | * | 5/2000 | Dubrow et al. | ............. 204/604 |
| 6,453,928 | B1 | * | 9/2002 | Kaplan et al. | ................. 137/14 |

FOREIGN PATENT DOCUMENTS

| DE | 19536103 | 4/1997 |
|---|---|---|
| EP | 0895120 | 2/1999 |
| WO | WO 97/00442 | 1/1997 |
| WO | WO 00/61275 | 10/2000 |

OTHER PUBLICATIONS

Branebjerg, et al., Fast mixing lamination, Feb. 2, 1996, Derwent Publication No. XP 000689310, pp. 441–446, Nordborg, Denmark.

* cited by examiner

*Primary Examiner*—A. Michael Chambers
(74) *Attorney, Agent, or Firm*—Garvey, Smith, Nehrbass & Doody, L.L.C.; Seth M. Nehrbass; Brett A. North

(57) ABSTRACT

A capillary reactor distribution device comprising first and second capillary pathways (2, 3) which meet at a junction (5) and a third capillary pathway (4) which leads away from the junction (5), the capillary pathways (2, 3, 4) being dimensioned such that, when first and second immiscible fluids (14, 15) are fed along respectively the first and second capillary pathways (2, 3) under predetermined laminar flow conditions, the first and second fluids (14, 15) chop each other into discrete slugs (16, 17) which pass along the third capillary pathway (4). Molecular mixing between the fluids (14, 15) takes place by way of axial diffusion between adjacent slugs (16, 17) and by way of internal circulation within each slug (16, 17) as the slugs (16, 17) progress along the third capillary pathway (4).

41 Claims, 6 Drawing Sheets

■ Liquid 1
□ Liquid 2

⊢ 0.3 mm

CAPILLARY REACTOR DISTRIBUTION DEVICE AND METHOD

The present invention relates to a capillary reactor distribution device and method and in particular to a distribution device and method for interfacing at least two immiscible fluids.

Improved methods of manufacturing at microscales have opened up new opportunities for the development of compact, efficient and highly controllable reactors. Rapid mass and heat transfer between fluids may now be engineered into reactors by the use of small dimensions for fluid transport. Short path lengths for thermal and molecular diffusion can provide an ideal environment for rapid exothermic/endothermic reactions while maintaining a laminar flow regime. Scale requirements for efficient mixing by diffusion can be calculated using the following equation (Crank, J., 1975, "The Mathematics of Diffusion", 2nd edition, Clarendon Press, Oxford):

$$d=(Fo.Dt)^{0.5} \quad (1)$$

where D is the diffusivity of the reacting molecules in the fluid, t is the residence time and Fo the Fourier number determining the level of mixing. For most systems, Fo=1 would be chosen. Reactions that may benefit most from this technique are those where phases cannot mix to form a single phase, such as liquid-gas, liquid-solid, gas-solid and immiscible liquid flow.

Two general methods are available for efficiently contacting two immiscible liquid streams within a microreactor. The first is the use of parallel liquid streams as described in WO 97/39814 and WO 99/22858 where diffusion is perpendicular to the flow direction. The second is the use of dispersed/continuous phase flow where one phase is in the form of small droplets within the other phase or slug flow where each phase is in the form of a series of slugs. Diffusive mass transfer may be aided by internal circulation within the droplets generated by the shear flow as demonstrated by Clift, R., Grace, J. R. and Weber, M. E. (1978, "Bubbles, drops and particles", Academic Press, New York).

Several benefits and drawbacks accompany these two techniques. In the use of parallel flow, it is difficult to achieve stability and similar residence times for liquids of significantly different viscosity or flow rate. On the other hand, for droplet flow, velocities of the dispersed and continuous phases remain similar, and a wider range of flow rate ratios can be tolerated. However, parallel flow has the advantage of easy bulk separation of the liquids after reaction, whereas droplets and slugs need to be separated by way of centrifugal or gravitational action.

Typical diffusion rates within liquids are in the range $10^{-8} m^2 s^{-1}$ to $10^{-9} m^2 s^{-1}$, and therefore, from equation (1) above, length scales for diffusion within the reactor are required to be of the order of 100 μm for rapid reactions requiring 1 to 10 s residence time. However, mass transfer enhancement due to internal vortices in droplet/slug flow augment this process and allow larger channel dimensions to be used while maintaining fast reaction times.

It is known from U.S. Pat. No. 5,921,678 to provide a microfluidic sub-millisecond mixer in which two capillary pathways meet head-on and in which a third capillary pathway leads away from the junction of the first two, thereby forming a T-junction. Two miscible fluids are then directed along the first two capillary pathways so as to meet at the junction, mix in turbulent conditions, and then flow along the third capillary pathway where reaction takes place. The third capillary pathway is very short, so as to constrain reaction time to sub-millisecond timescales, before the reactants are quenched and then separated. This prior art mixer is not suited for use with immiscible fluids.

According to a first aspect of the present invention, there is provided a capillary reactor distribution device comprising first and second capillary pathways which meet at a junction and a third capillary pathway which leads away from the junction, the capillary pathways being dimensioned such that, when first and second immiscible fluids are fed along respectively the first and second capillary pathways under predetermined laminar flow conditions, the first and second fluids chop each other into discrete slugs which pass along the third capillary pathway.

According to a second aspect of the present invention, there is provided a method for contacting two immiscible fluids, wherein a first fluid is fed under laminar flow conditions along a first capillary pathway and a second fluid is fed under laminar flow conditions along a second capillary pathway, the first and second capillary pathways meeting at a junction having a third capillary pathway leading away therefrom, and wherein the flow conditions in each of the first and second capillary pathways are selected such that the first and second fluids chop each other into discrete slugs which pass along the third capillary pathway.

In general, the two immiscible fluids are both in the liquid phase, although liquid/gas, solid/liquid/liquid and solid/liquid/gas reactions may be performed in the device and method of the present invention. In the case of solid/liquid/liquid and solid/liquid/gas reactions, the solid phase may be coated on a surface of the third capillary pathway, for example in the form of a catalyst coating for liquid/liquid or liquid/gas reactions.

In preferred embodiments, the first and second capillary pathways meet substantially head-on at the junction, although for some applications the first and second capillary pathways may be arranged to meet at angles other than substantially 180 degrees. For example, the first and second capillary pathways may be arranged to meet at an angle of substantially 90 degrees, at an angle between 90 and 180 degrees, or at an angle between 0 and 90 degrees. In some embodiments, the first and second capillary pathways may be arranged to meet at an angle of 90 degrees to 300 degrees, and the third capillary pathway may lie substantially midway between the first and second capillary pathways or at substantially 180 degrees to the first capillary pathway.

Advantageously, the capillary pathways are formed in or lined with a non-stick or low surface energy material, such as a fluoropolymer (e.g. PTFE or PVDF).

It is believed that the mechanism whereby the first fluid chops the second fluid into discrete slugs is as follows. Assuming that each fluid approaches the junction at a constant flow rate, and considering the case where the first and second capillary pathways meet substantially head-on, the first fluid flows preferentially into the third, exit capillary pathway while the second fluid forms an interface at the junction. The interface is moved into the third capillary pathway by the driving pressure from the first fluid supply aided by viscous shear from the second fluid. When the interface grows to a size that blocks the first fluid from entering the third pathway, the process switches and the second fluid flows preferentially into the third pathway while the first fluid forms an interface, which then moves into the third pathway before the process switches back again. This alternating flow of the first and second fluids generates a series of slugs in the third pathway. The lengths of the slugs is believed to be most significantly governed by the ratios of the widths of the inlet and outlet capillary pathways, the surface energy of the walls of the capillary pathways and the ratio of the first and second fluid flow rates. In particular, the ratio of slug lengths is generally substantially the same as the ratio of fluid flow rates. The lengths of the slugs are governed also to a lesser extent by the total fluid flow and the viscosities of the first and second fluids, and also by interfacial phenomena. Production of slugs is most preferably achieved in materials which do not have very low contact angles with either of the fluids.

As the slugs progress along the third capillary pathway, mixing of the first and second fluids on a molecular level is achieved by both axial diffusion between adjoining slugs and also by internal circulation within each slug, the latter process generally being the dominant one. Both forms of mixing will generally increase as slug length is reduced. For rapid mixing, the smallest slug length should be of the order of the width of the third capillary pathway, and the longest slug length not greater than 100 times the width thereof, and preferably not greater than 10 times the width thereof. It is particularly preferred that the longest slug length is not greater than twice the width of the third capillary pathway.

The device of the present invention may comprise a solid block of any appropriate material having the capillary pathways bored thereinto. Fluid may be pumped to the block and removed therefrom by way of standard capillary tubes which are connected to the capillary pathways bored into the block. The capillary tubes may connect to the capillary pathways at or near external surfaces of the block, or may connect thereto within the body of the block, near to the junction. Alternatively, passages may be bored into the block so as snugly to receive the capillary tubes, the junction being defined by the ends of the capillary tubes themselves where they meet within the block. Preferably, O-ring or similar seals are provided where the capillary tubes enter the block so as to prevent pressure losses as fluid is pumped towards the junction. Advantageously, the internal volume of the capillary pathways within the block is kept as small as possible.

Typical flow rates through the device of the present invention range from 10 nls$^{-1}$ to 100 µs$^{-1}$, with preferred flow rates ranging from 100 nls$^{-1}$ to 10 µls$^{-1}$. Flow rate ratios between the fluids in the first and second capillary pathways are advantageously not greater than 10:1 and are preferably close to unity for high mixing efficiency.

Alternatively, the device of the present invention may be formed by at least two generally laminar plates mounted one directly on top of the other such that a surface of one plate contacts a surface of the other plate, at least one of the surfaces being provided with features serving to define the capillary pathways. The plates will generally be in registration with each other. The at least one surface may include channels or ridge-like protrusions or both, such that when the surfaces of the plates are contacted, the required capillary pathways are defined between the plates. The channels and/or the protrusions may be formed by an etching process, or may be micromachined or moulded. Further plates with suitable surface features may be stacked on top of the at least two plates so as to produce a multi-layer device.

Either the first or the second capillary pathway or both may be provided with a fluid filter to help prevent stray particles from entering the device and which may block the capillary pathways. In the solid block embodiment of the present invention, the fluid filter is preferably located between either one or both of the input capillary tubes and the first or second capillary pathways.

The device and method of the present invention is particularly useful for conducting reactions between organic and aqueous liquids, for example the nitration of benzene and toluene as discussed hereinafter. Other applications include rapid mass transfer for liquid-liquid extraction and small volume reaction testing for analytical purposes.

For a better understanding of the present invention and to show how it may be carried into effect, reference shall now be made by way of example to the accompanying drawings, in which.

Figure 1:
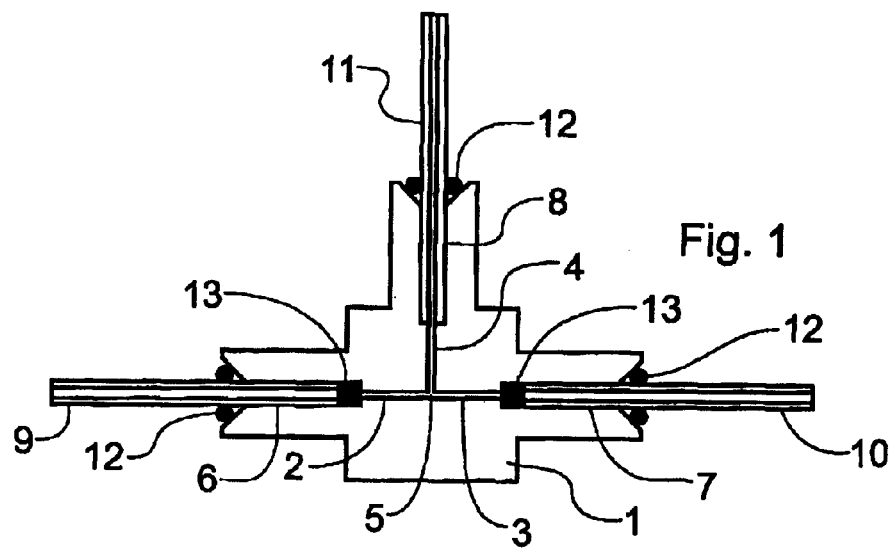
FIGS. 1 to 3 show three alternative configurations of the distribution device of the present invention.

FIG. 1 is a section through a PTFE block 1 into which first, second and third tubular capillary pathways 2, 3, 4 of diameter 0.5 mm and length 5 mm have been bored. The first and second capillary pathways 2, 3 meet head-on at a junction 5, and the third capillary pathway 4 leads away from the junction 5 substantially at right angles to the first and second capillary pathways 2, 3. Boreholes 6, 7, 8 are provided so as to allow PTFE capillary tubes 9, 10, 11 with internal diameters of 0.15 mm to be snugly inserted into the block 1 and to connect respectively to the capillary pathways 2, 3, 4. Each capillary tube 9, 10, 11 is provided with an O-ring seal 12 where it enters the block 1 so as to reduce pressure losses within the block 1, and filters 13 are provided where the feed capillary tubes 9, 10 connect with the first and second capillary pathways 2, 3.

Figure 2:
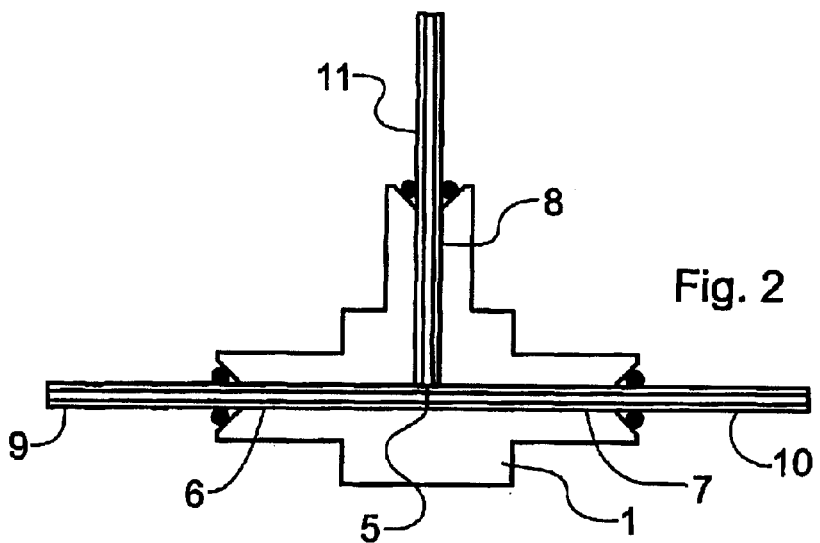

An alternative embodiment is shown in FIG. 2, where boreholes 6, 7, 8 extend to a middle portion of the block 1 so as to allow the capillary tubes 9, 10, 11 with internal diameters of 0.15 mm to meet and form the junction 5.

Figure 3:
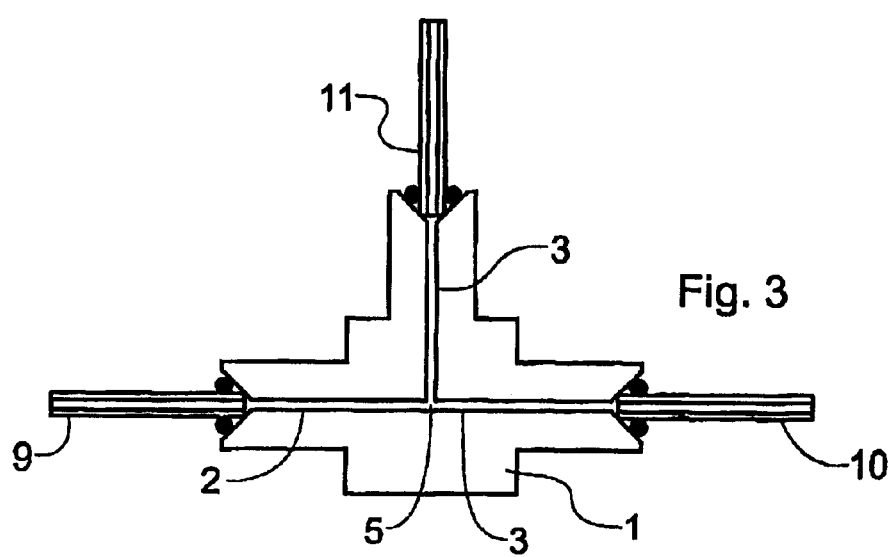

A further alternative embodiment is shown in FIG. 3, where the capillary pathways 2, 3, 4 of diameter 0.8 mm extend from the junction 5 to external surfaces of the block 1, where the capillary tubes 9, 10, 11 are connected.

It is to be noted that in some embodiments, the positions of capillary pathway 3 and capillary tube 10 may be swapped with those of capillary pathway 4 and capillary tube 11, such that the two feed capillary pathways 2, 3 meet substantially at right angles.

By using a syringe driver (not shown) to inject dyed kerosene 14 along capillary tube 9 and thence capillary pathway 2, and water 15 along capillary tube 10 and thence capillary pathway 3, a series of slugs 16, 17 were formed in capillary pathway 4 and thence capillary tube 11, as shown in FIGS. 4 to 7 and 8.

Figures 4, 5, 6:
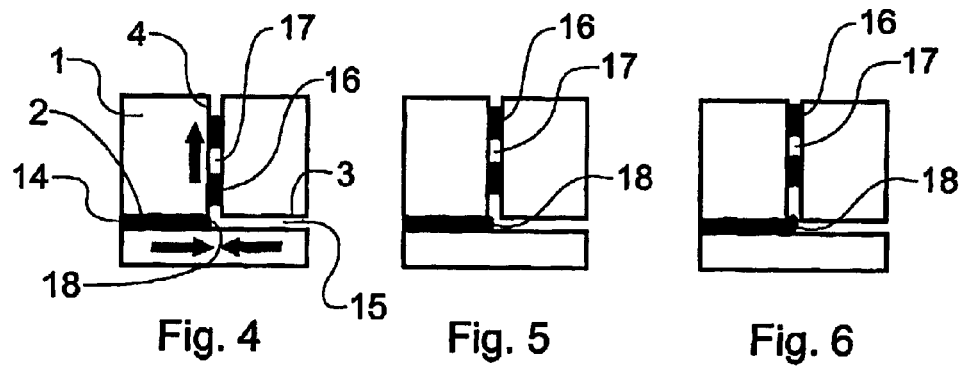
FIGS. 4 to 7 show a proposed mechanism for slug formation within the device of the present invention.
Figure 7:
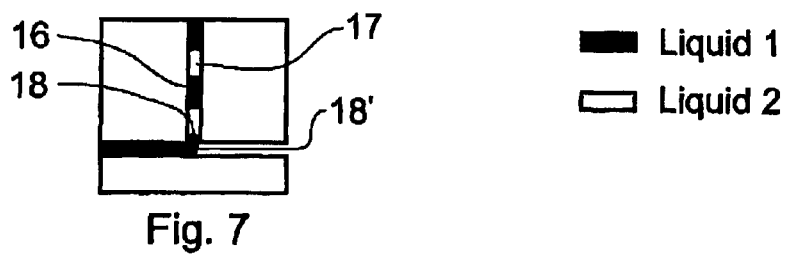
Figure 8:
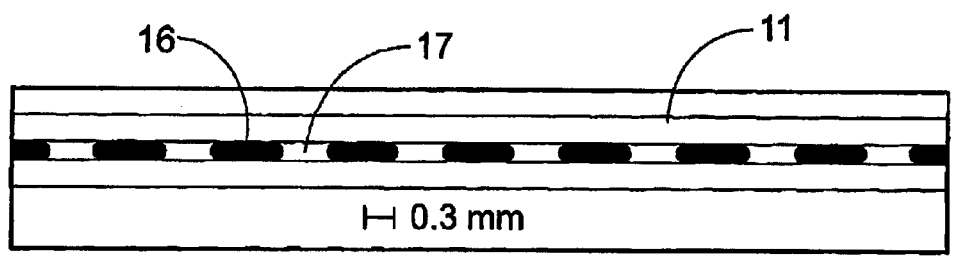
FIG. 8 shows a series of liquid slugs within a capillary tube.

The mechanism for slug 16, 17 formation is shown in FIGS. 4 to 7. In FIG. 4, water 15 flows preferentially from the capillary pathway 3 into the capillary pathway 4, while kerosene 14 forms an interface 18 at the junction 5. Due to the driving pressure behind the kerosene 14, the interface 18 is moved into the junction 5 and towards the capillary pathway 4, aided by viscous shear from the water 15 as shown in FIGS. 5 and 6. When the interface 18 has completely moved into the capillary pathway 4, as shown in FIG. 7, the flow of water 15 is blocked and kerosene 14 then flows preferentially into the capillary pathway 4, with the water 15 forming an interface 18'. The process is then reversed until the interface 18' moves into the capillary pathway 4 and water 15 again flows preferentially into the capillary pathway 4. The alternating movement of the interface 18, 18' causes a series of kerosene slugs 16 and water slugs 17 to be formed in the capillary pathway 4 and thence the capillary tube 11 as shown in FIG. 8.

Flow rates of 0.8 to 13 $\mu ls^{-1}$ were tested, with aqueous/organic flow ratios of 2:1 and 1:1. The embodiment of FIG. 1 was found to produce slug 16, 17 lengths of 2.1 to 5.5 mm, that of FIG. 2 to produce lengths of 0.3 to 0.9 mm and that of FIG. 3 to produce lengths of 18 to 30 mm. This indicates that the low internal flow volume of the FIG. 2 embodiment helps to produce short slug 16, 17 lengths.

Figure 9:
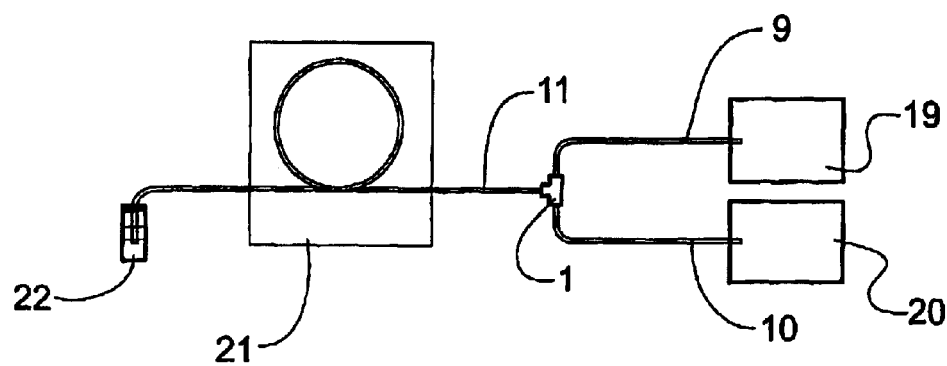
FIG. 9 shows a capillary reactor including a device of the present invention.

FIG. 9 shows a reactor comprising an aqueous phase pump 19 and an organic phase pump 20, respectively connected to capillary tubes 9, 10 which then pass into a distribution device 1 of the type shown in FIG. 2. An output capillary tube 11 passes from the device 1 and through a heater 21, inside which the capillary tube 11 is coiled for efficient use of space. The capillary tube 11 then passes from the heater 21 to a collection bottle 22. In the following examples, an aqueous phase reactant was pumped by pump 19 along capillary tube 9 and an organic phase reactant by pump 20 along capillary tube 10. Slugs (not shown) of aqueous phase and organic phase reactant were formed in the capillary tube 11 by the device 1, and then passed along the capillary tube 11, through the heater 21 and thence to the collection bottle 22 which contained solvents to halt the reaction between the reactants and to dilute the organic phase reactant. Analysis of the organic conversions discussed in the following examples was performed using gas chromatography.

EXAMPLE 1

Benzene Nitration

Distributors having capillary tubes made out of 316 stainless steel with respectively 127 μm, 178 μm and 254 μm bore sizes were constructed. A syringe driver was used to supply the liquids for the reaction and a heating, bath was used to control the reactor temperature. The nitration reaction involved contacting a stream of benzene with a stream of nitric and concentrated sulphuric acids. Various acid strengths and reactor temperatures were used in the nitration work and comparisons made of the reaction rate and by-product formation. A shell reaction model was used in calculating the reaction rate for the process. This assumes that nitration takes place in a acid boundary layer surrounding the organic phase. For this model mass transfer into the region and kinetic reaction rate within the region are equally important in the overall observed rate. The resulting equation governing this process can be written as a $1.5^{th}$ order reaction, as shown in equation (2), where X is the proportion of the initial nitric acid remaining at time t.

$$\frac{dX}{dt} = -CX^{1.5} \quad (2)$$

The value of constant C is determined by the mass transfer rate into the reaction zone and kinetic reaction rate within the zone. Integration of equation (2) yields the following equation for nitric acid concentration at time t.

$$X = \left(1 + \frac{Ct}{2}\right)^{-2} \quad (3)$$

Figure 10:
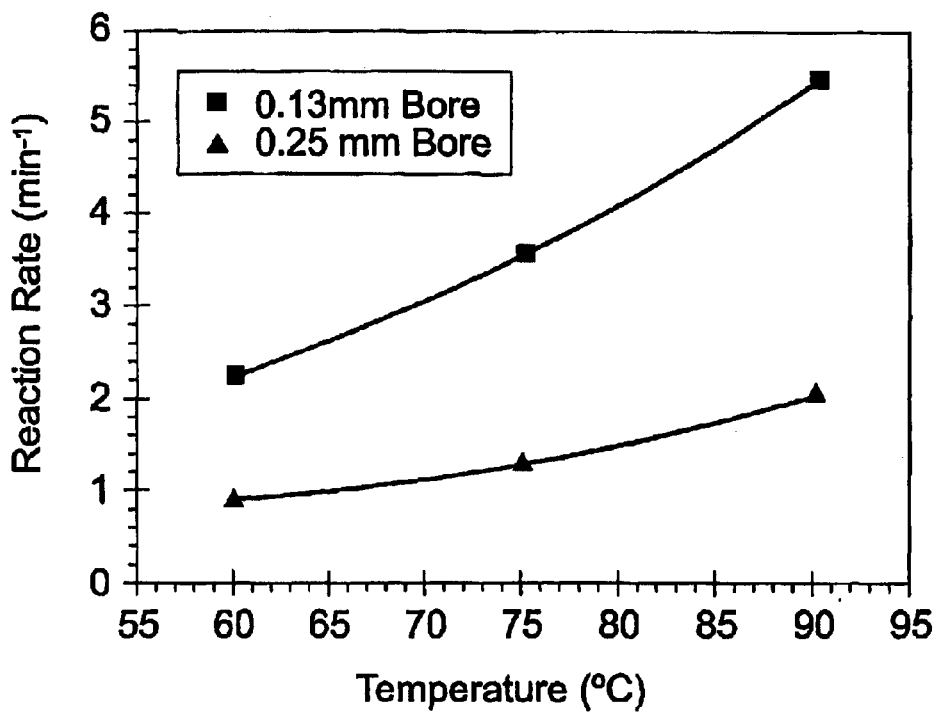
FIG. 10 is a graph of reaction rates against temperature for benzene nitration in the reactor of FIG. 9.

One method of characterising the nitration process is by comparison of the indicated initial reaction rates. This is defined as the reaction rate at the start of the process and can be calculated from equations (2) and (3) as, $$InitialRate = \frac{dX}{dt}\bigg|_{t=0} = C = \frac{2(X^{-1/2} - 1)}{t} \quad (4)$$

where X is the measured value at time t. A similar formula can be obtained for the organic reaction rate by substitution of X with the proportion of non-nitrated organic remaining. A comparison of the reaction rate observed for 127 μm and 254 μm bore capillary tubing under similar conditions is shown in FIG. 10. A high sulphuric acid concentration was used to ensure fast nitration kinetics and promote a mass transfer limited regime. Comparing the results for the two capillary diameters clearly shows enhanced performance at the smaller scale implying improved mixing.

Figure 11:
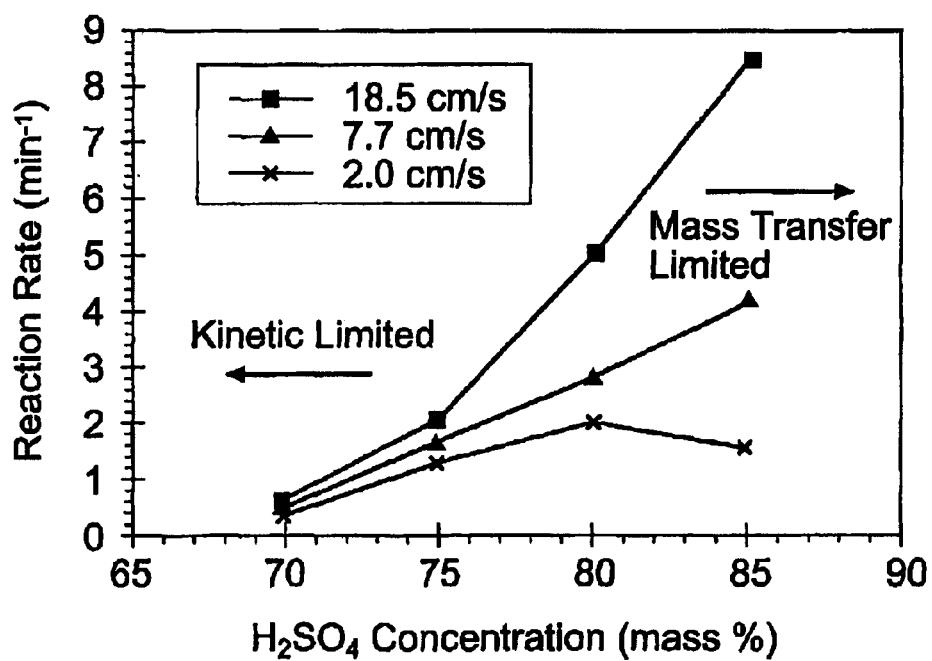
FIG. 11 is a graph of reaction rates for benzene nitration in the reactor of FIG. 9 at different flow velocities.

FIG. 11 illustrates the influence of capillary flow rate on organic reaction rate. An enhancement in reaction rate was observed when faster flow was applied to the reactor especially for the conditions with the fastest kinetics. This would indicate that increased velocity was leading to increased mixing. The primary source of this improvement is most likely due to increased internal circulation within the liquids, although some variation in slug length may also be contributing.

EXAMPLE 2

Toluene Nitration

Recent work has examined the nitration of toluene using a PTFE capillary reactor. The use of PTFE gave a more corrosion resistant system with less chance of blockage. Blockages were found to occur occasionally in the stainless steel system between runs probably due to sulphuric acid corrosion. However, no such problems occurred with the PTFE based system. Two HPLC pumps were used to supply the flow to the reactor with a greater run time capability.

Toluene nitration was performed using 150 μm bore tubing using a range of acid strengths and reactor temperatures. Results showed a lower influence of temperature on reaction rate than benzene nitration when temperatures of greater than 75° C. were used. Typical nitric acid reaction rates for the system are shown in Table 1 for a range of acid and organic flow ratios. Observed rates were generally higher than for benzene under similar conditions.

TABLE 1

Initial nitric acid reaction orates for toluene nitration in a 150 μm PTFE reactor. (Experiments used 78% $H_2SO_4$ with 7% $HNO_3$)

| Acid:Organic Flow Ratio | Reaction Rate at 25° C. (min$^{-1}$) | Reaction Rate at 60° C. (min$^{-1}$) |
|---|---|---|
| 2:1 | 3.27 | 6.10 |
| 3:1 | 2.81 | 6.12 |
| 5:1 | 2.25 | 4.39 |
| 7:1 | 1.65 | 4.17 |

Figure 12:
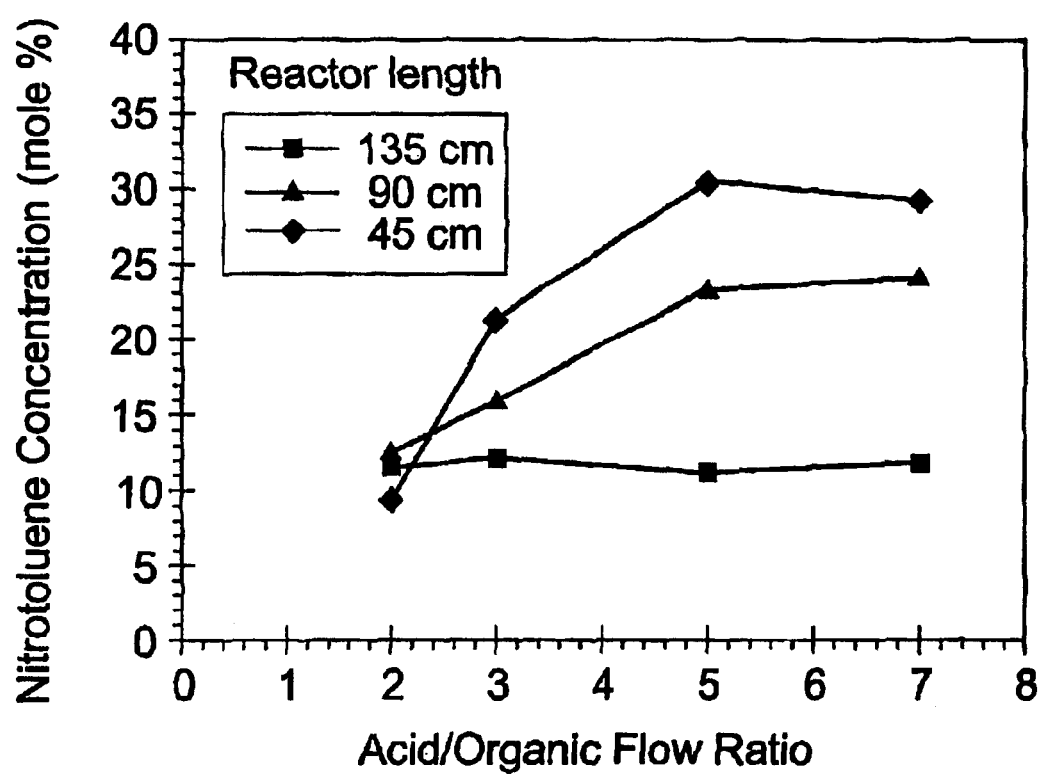
FIG. 12 is a graph of nitrotoluene concentration against acid/organic flow ratio for toluene nitration along different reaction pathway lengths in the reactor of FIG. 9.

FIG. 12 shows nitrotoluene production for a range of flow ratios and reactor lengths. The results show an increasing production of nitrotoluene when larger ratios of acid to organic were used in the reactor. However, the little improvement in conversion is observed for flow ratios exceeding 5:1 even though more acid is available for nitration. This is also reflected in the lower reaction rates shown in Table 1 for the higher flow ratios. This would suggest a poorer mixing environment for the high flow ratios probably due to increased acid slug length.

End effects from possible post reactor nitration were also examined for both benzene and toluene nitration. Output from reactor tubes of different lengths were compared to check that increased length provided higher conversion implying that the reaction was taking place within the capillary tube and not within the sampling system. FIG. 12 shows the results from three different reactor lengths using the same conditions and shows in general that higher conversion was achieved for the longer tubes.

Visual analysis of liquid-liquid flow through a capillary reactor has shown that a pattern of alternating organic/aqueous slugs can be produced each having lengths down to 300 μm. The work has also shown the importance of low internal volumes in distributor design for controlling the pattern of liquid-liquid flow produced.

Reaction results for benzene and toluene nitration have indicated reaction rates in the range of 1 to 8 min$^{-1}$ can be produced from a capillary reactor. This would indicate residence times for complete conversion to be in the region of 10 to 60 seconds. A comparison with some existing benzene nitration processes (as described in the indicated U.S. patents) is shown in Table 2. This illustrates that even with 178 μm bore tubing the capillary reactor process is competitive.

the liquids into smaller slugs or droplets. Scale-up of the devices for chemical production will be achieved through use of parallel channels whilst their use for analysis will be facilitated through small on-chip versions.

Figure 13:
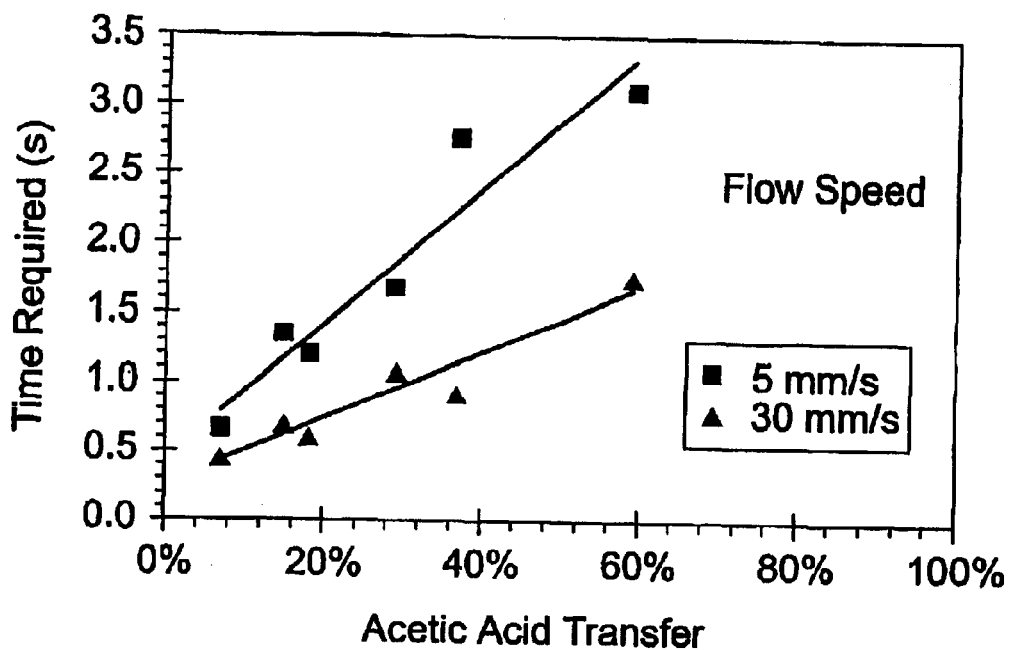
FIG. 13 is a graph of transfer times for acetic acid from organic to aqueous phase in a 0.38 mm×0.38 mm glass channel.

Referring now to FIG. 13, there is shown an alternative embodiment of the present invention comprising two laminar plates 40, 41 which are mountable one 40 on top of the other 41 such that the plates 40, 41 are in registration with each other. The plates 40, 41 are made out of a non-stick material such as PTFE, and an upper surface 42 of plate 40 is provided with etched channels defining capillary pathways 43, 44, 45 which meet at a junction 46. Input capillary pathways 43, 44 meet substantially head-on at the junction 46, and output capillary pathway 45 leads away therefrom substantially at right angles to the capillary pathways 43, 44. The other plate 41, when mounted on top of plate 40, provides a top surface for the capillary pathways 43, 44, 45. The plate 41 may be secured to the plate 40 by way of welding, adhesives, mechanical clamps or other suitable means.

EXAMPLE 3

Acetic Acid Titration

Figure 14:
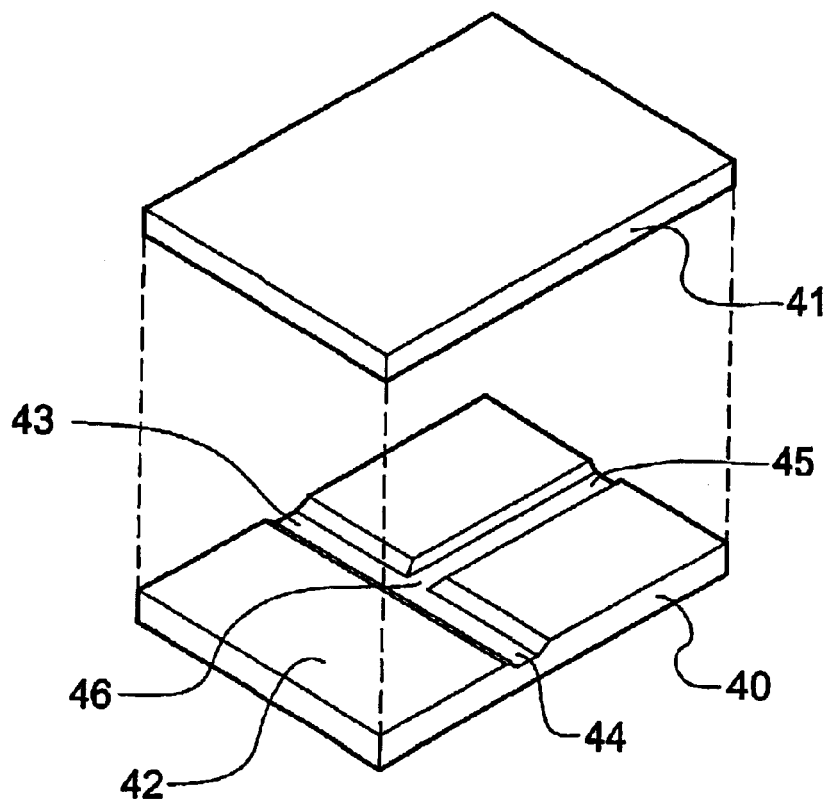
FIG. 14 shows an alternative embodiment of the device of the present invention.

Mass transfer performance of a glass capillary reactor distribution device having capillary pathway channels 0.38 mm wide and 0.38 mm deep in a standard configuration, as shown for example in FIG. 13, was examined using a titration reaction. Kerosene loaded with 0.65 moles per liter of acetic acid was used in conjunction with an aqueous solution of sodium hydroxide at various concentrations of NaOH and containing phenol red pH indicator. Equal flow rates of each liquid phase were fed through the glass device and the time taken to transfer different quantities of acetic acid, as indicated by colour change in the aqueous system, was measured at two different flow velocities. Typical slug lengths produced were 1.1 mm to 1.6 mm long. The results are shown in FIG. 14. These show a significant enhancement in performance gained by vortex mixing inside the slugs, compared with that expected from pure diffusion at this scale, and also that higher flow velocity produces faster mass transfer.

Figure 15:
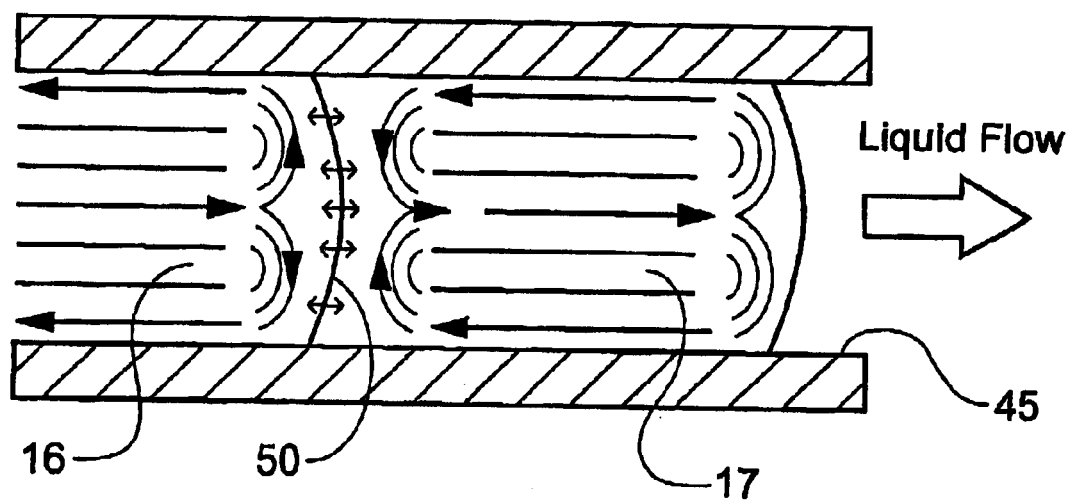
FIG. 15 shows the flow dynamics of slug propagation along a capillary pathway.

Finally, FIG. 15 illustrates the flow dynamics of a pair of slugs 16, 17 passing along a capillary pathway 45 of a device as shown in FIG. 14. The general flow direction is indicated by arrow A, with the internal circulation patterns being

TABLE 2

Comparison of benzene nitration performance with existing processes

| Information source | Inlet (° C.) | Outlet (° C.) | $H_2SO_4$ (mass %) | Conversion (%) | By-product (ppm) | Time (s) | Rate (min$^{-1}$) |
|---|---|---|---|---|---|---|---|
| US 4,091,042 | 80 | 128 | 60.6 | 89.5 | 1000 | 120 | 0.9 |
| US 4,091,042 | 80 | 134 | 65.2 | 99.1 | 2090 | 120 | 2.1 |
| US 5,313,009 | 95 | 120 | 69.5 | 90 | 1750 | 25 | 4.6 |
| Capillary 178 μm | 90 | 90 | 77.7 | 94.0 | 4600 | 24.4 | 5.90 |
| Capillary 178 μm | 90 | 90 | 72.2 | 60.7 | Below 1000 | 26.1 | 1.6 |

Ultimately, narrow channel microreactors based on this technique of liquid-liquid contacting will require shorter path lengths for diffusion to improve efficiency and lower by-product production. The use of microfabricated devices with more sophisticated distribution will be required to chop shown for each slug 16, 17, these patterns being caused by friction between the walls of the pathway 45 and boundary layers of the slugs 16, 17 as they progress along the pathway 45. Inter-slug diffusion occurs at an interface 50 between the slugs 16, 17.

| Nomenclature | | |
|---|---|---|
| C | Reaction rate constant | $s^{-1}$ |
| D | Diffusivity | $m^2 \cdot s^{-1}$ |
| d | Path length for diffusion | m |
| Fo | Fourier number | — |
| t | Residence time | s |
| X | Proportion of nitric acid remaining | — |

What is claimed is:

1. A method for contacting two immiscible fluids, wherein a first fluid is fed under laminar flow conditions along a first capillary pathway and a second fluid is fed under laminar flow conditions along a second capillary pathway, the first and second capillary pathways meeting at a junction having a third capillary pathway leading away therefrom, and wherein the flow conditions in each of the first and second capillary pathways are selected such that the first and second fluids are fed continuously and simultaneously alone the first and second capillary pathways, the first and second fluids chop each other into discrete slugs which pass along the third capillary pathway.

2. A method according to claim 1, wherein the first and second capillary pathways meet substantially head on.

3. A method according to claim 1, wherein the first and second capillary pathways meet substantially at right angles.

4. A method according to claim 1, wherein the first and second capillary pathways meet at an angle between 90 and 180 degrees.

5. A method according to claim 1, wherein the first and second capillary pathways meet at an angle between 0 and 90 degrees.

6. A method according to claim 1, wherein the first and second capillary pathways meet at an angle from 90 to 300 degrees.

7. A method according to claim 1, wherein the fluids are both liquids.

8. A capillary reactor distribution device comprising first and second capillary pathways which meet at a junction and a third capillary pathway which leads away from the junction, an aqueous phase pump operatively connected to the first capillary pathway, an organic chase pump operatively connected to the second capillary pathway, the capillary pathways being dimensioned such that, when first and second immiscible fluids are fed along respectively the first and second capillary pathways by the respective pumps at flowrates between about 10 nl/s to 100 µl/s, the first and second fluids chop each other into discrete slugs which pass along the third capillary pathway.

9. A device as claimed in claim 8, wherein the first and second capillary pathways meet substantially head on.

10. A device as claimed in claim 9, comprising at least two generally laminar plates mounted one directly on top of the other such that a surface of one plate contacts a surface of the other plate, at least one of the surfaces being provided with features serving to define the capillary pathways.

11. A device as claimed in claim 8, wherein the first and second capillary pathways meet substantially at right angles.

12. A device as claimed in claim 8, wherein the first and second capillary pathways meet at an angle between 90 and 180 degrees.

13. A device as claimed in claim 8, wherein the first and second capillary pathways meet at an angle between 0 and 90 degrees.

14. A device as claimed in claim 8, wherein the first and second capillary pathways meet at an angle from 90 to 300 degrees.

15. A device as claimed in any preceding claim, comprising a solid block into which the capillary pathways have been bored or otherwise formed.

16. A device as claimed in claim 15, wherein the solid block is made out of a non-stick material.

17. A device as claimed in claim 16, wherein the solid block is made out of a material having a low surface energy.

18. A device as claimed in claim 16, wherein the capillary pathways extend from an interior portion of the solid block towards an outer surface thereof, and wherein attachment means are provided for attaching external capillary tubes to the capillary pathways.

19. A device as claimed in claim 15, wherein the solid block is made out of a material having a low surface energy.

20. A device as claimed in claim 19, wherein the capillary pathways extend from an interior portion of the solid block towards an outer surface thereof, and wherein attachment means are provided for attaching external capillary tubes to the capillary pathways.

21. A device as claimed in claim 15, wherein the capillary pathways are lined with a non-stick material.

22. A device as claimed in claim 21, wherein the capillary pathways are lined with a material having a low surface energy.

23. A device as claimed in claim 21, wherein the capillary pathways extend from an interior portion of the solid block towards an outer surface thereof, and wherein attachment means are provided for attaching external capillary tubes to the capillary pathways.

24. A device as claimed in claim 15, wherein the capillary pathways are lined with a material having a low surface energy.

25. A device as claimed in claim 24, wherein the capillary pathways extend from an interior portion of the sold block towards an outer surface thereof, and wherein attachment means are provided for attaching external capillary tubes to the capillary pathways.

26. A device as claimed in claim 15, wherein the capillary pathways extend from an interior portion of the solid block towards an outer surface thereof, and wherein attachment means are provided for attaching external capillary tubes to the capillary pathways.

27. A device as claimed in claim 26, wherein the attachment means are located on an outer surface of the solid body.

28. A device as claimed in claim 26, wherein the attachment means are located or extend within the solid block.

29. A device as claimed in claim 26, wherein the attachment means include O-ring seals.

30. A device as claimed in claim 29, wherein the capillary pathways are defined by capillary tubes inserted into boreholes provided in the solid block and positioned so that mutually abutting ends of the capillary tubes form the junction.

31. A device as claimed in claim 28, wherein the capillary pathways are defined by capillary tubes inserted into boreholes provided in the solid block and positioned so that mutually abutting ends of the capillary tubes form the junction.

32. A device as claimed in claim 8, comprising at least two generally laminar plates mounted one directly on top of the other such that a surface of one plate contacts a surface of the other plate, at least one of the surfaces being provided with features serving to define the capillary pathways.

33. A device as claimed in claim 32, wherein the surface features comprise channels.

34. A device as claimed in claim 32, wherein the surface features comprise ridge-like protrusions.

35. A device as claimed in claim 32, wherein the plates are made of a non-stick material.

36. A device as claimed in claim 32, wherein the plates are made of a material having a low surface energy.

37. A device as claimed in claim 32, wherein the contacting surfaces of the plates are coated with a non-stick material.

38. A device as claimed in claim 32, wherein the contacting surfaces of the plates are coated with a material having a low surface energy.

39. A device as claimed in claim 8, wherein at least one of the first and the second capillary pathways is provided with a filter.

40. A device as claimed in claim 8, wherein at least one of the first, second or third capillary pathways is lined with a chemically reactive material.

41. A device as claimed in claim 40, wherein the material is a solid heterogeneous catalyst.

* * * * *